United States Patent
Wakikaido et al.

(10) Patent No.: US 6,428,535 B1
(45) Date of Patent: Aug. 6, 2002

(54) DISPOSABLE MEDICAL INSTRUMENT AND MEDICAL DEVICE INCORPORATING THE INSTRUMENT

(75) Inventors: Koichi Wakikaido, Osaka; Suminori Kitada, Saitama, both of (JP)

(73) Assignee: Azwell Inc., Osaka (JP)

( * ) Notice: Subject to any disclaimer, the term of this patent is extended or adjusted under 35 U.S.C. 154(b) by 0 days.

(21) Appl. No.: 09/555,966
(22) PCT Filed: Oct. 6, 1999
(86) PCT No.: PCT/JP99/05526
§ 371 (c)(1), (2), (4) Date: Jun. 7, 2000
(87) PCT Pub. No.: WO00/21448
PCT Pub. Date: Apr. 20, 2000

(30) Foreign Application Priority Data

Oct. 9, 1998 (JP) ............................................. 10-287503

(51) Int. Cl.[7] ............................................... A61B 18/18
(52) U.S. Cl. ............................... 606/32; 606/34; 606/1
(58) Field of Search .............................. 606/32, 33, 41, 606/48, 50, 1; 128/908

(56) References Cited

U.S. PATENT DOCUMENTS 5,359,993 A * 11/1994 Slater et al. ................. 606/205
5,817,092 A * 10/1998 Behl ............................. 606/41
5,935,126 A *  8/1999 Riza ............................. 606/51

FOREIGN PATENT DOCUMENTS

| JP | 62-139643 | 6/1987 |
| JP | 2-215450 | 8/1990 |
| JP | 4-323571 | 11/1992 |
| JP | 5-332535 | 12/1993 |
| WO | 96-04936 | 2/1996 |

* cited by examiner

Primary Examiner—Linda C. M. Dvorak
Assistant Examiner—David M. Ruddy
(74) Attorney, Agent, or Firm—Millen, White, Zelano & Branigan, P.C.

(57) ABSTRACT

A medical apparatus comprising an apparatus body and a terminal instrument which operates when receiving a terminal output which is an electric or electromagnetic output. The terminal instrument is provided with an installed cell of predetermined capacity and the apparatus body is provided with a circuit for measuring the electromotive force (emf) of the installed cell while discharging the emf via a predetermined resistance as the terminal instrument is used. A comparator compares the emf with a standard voltage and the output command is blocked from the primary control section when the emf of the installed cell is below the standard voltage. Moreover, an alarm is generated when the emf of the installed cell is below the standard voltage level during the use of the terminal instrument.

18 Claims, 4 Drawing Sheets

DISPOSABLE MEDICAL INSTRUMENT AND MEDICAL DEVICE INCORPORATING THE INSTRUMENT

TECHNICAL FIELD

The present invention relates to a medical apparatus consisting of a terminal instrument for giving certain treatment to the body with electric or electromagnetic output and an apparatus body for activating the terminal instrument. More specifically, the present invention relates to a disposable medical instrument which is activated by electric or electromagnetic output and equipped with a mechanism that prohibits its reuse after a predetermined length of use, as well as to an apparatus body for activating it, and to a medical apparatus consisting of them.

BACKGROUND ART

Many of medical instruments to be brought into direct contact with the body or body fluid are supplied as disposable items for prevention of inter-patient infection. As to an apparatus for coagulation or hemostasis of bio-tissues like a microwave surgical apparatus, too, not a few probes to be brought into contact with the body are supplied as disposable items. In some hospitals or like facilities, however, some cases have been noted where such medical instruments are repeatedly used in order for cost reduction or otherwise. Such a way of use may put patients at risk of infection. Further, as they are instruments designed to be disposable, they may degrade through repeated uses and thereby slump into malfunction just while they are being used.

In order to avoid such problems, it has been attempted to design a medical instrument so that it cannot be used beyond predetermined times or length. For example, an instrument once used will, without doubt, be washed if it is about to be used again. Based on this, a technique is disclosed in Japanese Laid-open Patent Publication H07-95982 by which some element of a probe or a like instrument is made of a material comprising a hydrophilic polymer, which is dissolved, swollen or soften through washing and thereby blocks the reuse of the instrument. Another device is also known with which the reuse of a probe is prevented by forcibly melting down a fuse installed in the probe at the end of its use.

With the method by which some element of the instrument is made of a material comprising a hydrophilic polymer, however, there is a great disadvantage that the instrument could become unusable even during a surgical operation, too, due to its dissolution, swelling or softening when it is brought into prolonged contact with blood, a disinfectant solution or physiological saline. Likewise, with the method relying on a fuse installed in the probe, there is a risk that the body would receive an electric shock, for an electric current, which is not less than 100 mA, for example, must be supplied to the probe by the apparatus body to forcibly melt down the fuse.

Upon the above background, the objective of the present invention is to provide a medical instrument and a medical apparatus equipped with it for microwave surgery, electric knife surgery, laser knife surgery, argon beam coagulation, etc., wherein the medical instrument is made so that it can substantially force itself to be disposed of after use through restricting, without adversely affecting its quality or safety of the apparatus, the length of time during which the use of the medical instrument is allowed by installing in the medical instrument, e.g., a probe, which is brought into direct contact with the body or body fluid of patients a mechanism that limits the operative life span of the instrument.

DISCLOSURE OF INVENTION

Thus, the present invention provides a medical apparatus comprising:

an apparatus body having a terminal-output-generating section which generates predetermined terminal output which may be electric or electromagnetic output and a primary control section which sends an output command to make the terminal-output-generating section generate terminal output, and a terminal instrument which is removably connected via a cable to the terminal-output-generating section and operates as predetermined while receiving the terminal output wherein:

(1) the terminal instrument is provided with an installed cell of predetermined capacity and further provided with terminals respectively extending from the both poles of the installed cell and electrically connected via a cable to respective cell-voltage-input terminals on the apparatus body, and (2) the apparatus body is provided with (a) an allowable-length-of-use-setting/discharging section and an extension-of-time-setting section both of which operate upon receipt of the output command from the primary control section, as well as with a comparison-and-determination section, a standard-voltage-setting section which provides the comparison-and-determination section with standard-voltage information to be referred, and an alarm-generating section, wherein:

(b) the allowable-length-of-use-setting/discharging section is so constructed that it, upon receipt of the output command, provides electrical connection between the cell-voltage-input terminals via a predetermined resistor to form a closed circuit to discharges the installed cell and sends a voltage-information output corresponding to the electromotive force of the installed cell, which is derived based on the voltage between two points within the circuit, to the comparison-and-determination section, (c) the comparison-and-determination section is so constructed that it compares the voltage-information output with the standard-voltage information received from the standard-voltage-setting section and determines whether the electromotive force of the installed cell is on or above the standard level or it has fallen below the standard level, and transmits the result signal to the extension-of-time-setting section and the alarm-generating section, (d) the extension-of-time-setting section is so constructed that it, upon receipt of the signal from the comparison-and-determination section, transmits the output command received from the primary control section to the terminal-output-generating section if the electromotive force of the installed cell is on or above the standard level but can block the output command if the electromotive force of the installed cell is below the standard level, (e) the alarm-generating section is so constructed that it, corresponding to the result signal received from the comparison-and-determination section, generates an alarm to indicate the result if the electromotive force of the installed cell is lower than the standard level, and (f) the allowable-length-of-use-setting/discharging section is so constructed that it keeps discharging the installed cell while the output command from the primary control section is transmitted to the terminal-output-generating section and the terminal-output-generating section is generating terminal output.

The present invention with the above features is characterized in that the installed cell is discharged and wasted via the apparatus body while the terminal instrument is in actual use (e.g., by supplying microwave to the electrodes of a microwave surgery apparatus). The electromotive force of the cell installed in the terminal instrument thus falls below the standard level after a certain length of use. When a terminal instrument with an installed cell whose electromotive force is below the standard level is attached to the apparatus body and set to be energized in order to reuse it, the comparison-and-determination section determines that the electromotive force of the installed cell is below the standard level. This result in the output command from the primary control section being blocked and not transmitted to the terminal-output-generating section. Thus, terminal output is not generated and such a improper use therefore is effectively prevented. In addition, the user is notified with an alarm that it would be an improper use. Thus, by preventing reuse of the terminal instrument, the apparatus of the present invention guarantees that the instrument be properly used as a disposable item as originally intended, thereby preventing inter-patient infection via the instrument.

The medical instrument according to the present invention does not employ a hydrophilic polymer material or a fuse to be melted down as employed in the prior art. Thus, the present instrument free of risks of becoming unusable during use due to swelling or softening, or of giving an electric shock to the patient, and therefore it is safer than those of the prior art.

In the specification, "electric or electromagnetic output" includes, but is not limited to, direct current, alternating current, high-frequency current, microwave, and laser.

Further, in the specification, "cable" means any of physical means in general for transmitting terminal output and is not limited to a cable of a particular structure.

Still further, in the specification, to "operate as predetermined" means to function as intended for the terminal instrument corresponding to the respective types of terminal output including, but not limited to, microwave radiation, arc discharge, and laser radiation.

Therefore, in the specification, "medical apparatus" includes in general a variety of medical apparatus "comprising: an apparatus body having a terminal-output-generating section which generates predetermined terminal output which may be electric or electromagnetic output and a primary control section which sends an output command to make the terminal-output-generating section generate terminal output, and a terminal instrument which is removably connected via a cable to the terminal output generating section and operates as predetermined while receiving the terminal output". Typical examples of such a "medical apparatus" include, but are not limited to, an apparatus for microwave surgery, electric knife surgery, laser knife surgery or argon beam coagulation. The terminal instrument is one of those adapted to such an apparatus including, but not limited to, microwave electrodes, an electric knife, a laser knife, or an argon beam coagulation probe.

The cell installed in the terminal instrument, which is a component of the apparatus of the present invention, is used to set the operative life span of the terminal instrument. Considering the length of time during which the terminal instrument is used in one treatment procedure of a usual case, a "predetermined duration of discharge" may be set so that the cell is used up during use of the instrument in a usual manner through a single treatment procedure. In the case of a microwave treatment apparatus, it may be set at a value of about several to ten-odd minutes, for example, before shipment. The load resistance of the circuit used for discharge, as well as the capacity of the installed cell, may be selected as desired, without particular limitation, so that the cell will be used up within the predetermined length of time without excessive heat generated during discharge. As for the installed cell, it may be of any of proper types and not limited to particular ones. However, a preferred type of cells are such that they can keep the electromotive force relatively constant during discharge just until the complete waste is reached. This is because such a type of cells allow an easy and reliable determination of the lapse of the operative life span of the terminal instrument in use with a simple, convenient structure of circuit A preferable example of such a type of cells is a silver oxide cell.

In the present invention, an "output command" is generated by the primary control section in response to a predetermined operation by a user and transmitted to the allowable-length-of-use-setting/discharging section and the extension-of-time-setting section. The allowable-length-of-use-setting/discharging section is so made that it discharges the cell via a predetermined resistor upon receipt of the output command and, while thereby wasting the cell over a predetermined span of time, measures the electromotive force of the installed cell by some proper circuit and sends a corresponding voltage-information output to the comparison-and-determination section. An allowable length of use can be set by properly adjusting resistance, which preferably is set before shipment in a manner that prohibits any arbitrary alteration by a user. The electromotive force of the installed cell can be readily derived based on the voltage between two points in the circuit and the electrical properties known of the circuit, though any other means may be employed. Insofar as it is compatible with the comparison-and-determination section, the "voltage-information output" may be given in any form such as the voltage corresponding to the electromotive force of the installed cell, or digital data indicating the electromotive force of the installed cell, or the like.

The comparison-and-determination section is constructed using any proper comparator circuit compatible with the allowable-length-of-use setting/discharging section, for which known means may be used as desired.

The standard-voltage-setting section provides standard-voltage information based on which the comparison-and-determination section determines whether or not the cell is used up, which information, as is the above form of the voltage-information output, is any form compatible with the comparison-and-determination section. Where a silver oxide cell is employed, with a load resistor selected to cause complete discharge in ten-odd minutes, for example, the discharging cell keeps its cell voltage at about 1.4–1.3 V just until the complete waste is reached, and the cell voltage sharply lowers when completely wasted. Therefore, a standard voltage of 1 V, for example, allows an easy determination of when the cell is used up. Alternatively, in accordance with the installed cell and the structure of the circuit employed, more than one standard voltages may be set, such as a first standard voltage for detecting when complete waste of the installed cell is approaching, and a second standard voltage, which is lower than the former, for detecting the complete waste of the installed cell. In such an arrangement, the standard voltages may be utilized to let the comparison-and-determination section, the extension-of-time-setting section and the alarm-generating section to operate in association in such a manner that a corresponding signal is sent to the alarm-generating section when the cell voltage comes down below the first standard voltage, and thereby a provisional alarm is generated which predicts the approach of the cell's use up, and, only when the cell voltage has fallen below the second standard voltage, the output command is blocked and an alarm is activated telling the shut down of the output.

The extension-of-time-setting section is constructed using any proper circuit provided that it serves as a gate which, according to the result signal received from the comparison-and-determination section, transmits the output command to the terminal-output-generating section if the electromotive force of the installed cell is on or above the predetermined standard voltage but blocks the output command if the electromotive force of the installed cell is lower than the standard level (the standard voltage). As described later, the extension-of-time-setting section may, as desired, have an additional function that can extend the allowable length of use of the terminal instrument while it is being used.

The alarm-generating section may be so constructed that it, according to the result signal received (directly or indirectly, via the extension-of-time-setting section) from the comparison-and-determination section, generates an alarm which allows for the user to readily realize the condition of the terminal instrument if the electromotive force of the installed cell is below the standard level (the standard voltage), which alarm may be an optical and/or auditory alarm, e.g., a yellow or red lamp which is lit or blinks, an interrupted or continuous sound, or displayed characters of "Warning" or "Stop Using".

The present invention also provides a medical apparatus as above described and further characterized in that:

(g) the extension-of-time-setting section is so constructed that it, while the output command from the primary control section is transmitted to the terminal-output-generating section and the terminal-output-generating section is thereby generating terminal output, continually sends the voltage-information output corresponding to the electromotive force of the installed cell to the comparison-and-determination section, (h) the comparison-and-determination section is so constructed that it compares the continually received voltage-information output with the standard-voltage information received from the standard-voltage-setting section, thereby continually determines whether the electromotive force of the installed cell is on or above the standard level or has come down below the standard level, and transmits the result signal to the extension-of-time-setting section and the alarm-generating section, (i) the extension-of-time-setting section is so constructed that it, upon receipt of the signal in (h), continues to transmit the output command received from the primary control section to the terminal-output-generating section if the electromotive force of the installed cell is on or above the standard level, but can block the output command if the electromotive force of the installed cell has come down below the standard level, and (j) the alarm-generating section is so constructed that it, corresponding to the signal in (h), can generate an alarm indicating when the electromotive force of the installed cell has come down below the standard revel.

The apparatus with the above features can make the terminal instrument unusable when the installed cell is wasted through the use of the terminal instrument beyond a predetermined allowable length of time even while the terminal output is being generated. With this apparatus, a terminal instrument once used causes higher probability that it, if reused, is made unusable just while it is being reused, for its installed cell's capacity has been decreased even if not completely wasted. This apparatus, therefore, can effectively prevent reuse of the terminal instrument once used.

Furthermore, the present invention provides a medical apparatus with the above features of (a) to (j) which can make the terminal instrument unusable while the terminal output is being generated when the installed cell is wasted through the use of the terminal instrument beyond a predetermined allowable length of time, which is further characterized in that the extension-of-time-setting section is provided with a timer mechanism which is turned on when the electromotive force of the installed cell has come down below the standard level in (h), and that the primary control section, the allowable-length-of-use-setting/discharging section, the comparison-and-determination section and extension-of-time-setting section are mutually associated in such a manner that the output command being received from the primary control section is transmitted to the terminal-output-generating section without being blocked until the term set by the timer mechanism has lapsed.

Even when the installed cell is used up due to a prolonged use of the terminal instrument during a single treatment procedure, this apparatus allows to avoids any inconvenience of exchanging terminal instruments during the treatment by adjusting the timer mechanism to a proper length of time, for a permitted use of the terminal instrument is guaranteed for a predetermined length of time (three minutes, for example, in the case of a microwave treatment apparatus) after the use up of the installed cell. When the installed cell is used up during operation, the user is notified by the generated alarm that a short time is left for the permitted use of the same terminal instrument.

Furthermore, instead of employing such a timer mechanism as above, the apparatus may be so constructed that it does not block the output command while the terminal instrument is activated and block only a newly generated output command once the previous output command was halted. Thus, the present invention further provides a medical apparatus with the above features of (a) to (j) which can make the terminal instrument unusable while the terminal output is being generated when the installed cell is wasted through the use of the terminal instrument beyond a predetermined allowable length of time, which is further characterized in that the primary control section, the allowable-length-of-use-setting/discharging section, the comparison-and-determination section and extension-of-time-setting section are mutually associated in such a manner that, after the electromotive force of the installed cell has come down below the standard level in (h), the output command being received from the primary control section is transmitted to the terminal-output-generating section without being blocked until the output command is once halted.

With this apparatus, while the terminal output is being generated to activate the terminal instrument, the output command is transmitted to the terminal-output-generating section without being blocked to allow the terminal instrument to be kept activated insofar as the output command is continuously generated by the primary control section even if the installed cell has been used up. This apparatus therefore, allows a prolonged use of the terminal instrument without trouble of its being shut down just while it is in use. This situation is maintained until the output command is halted. Once the output command is halted, reuse of the terminal instrument is prohibited because a newly generated output command would be blocked in the extension-of-time-setting section and no terminal output would thus be generated, for the comparison-and-determination section determines that the electromotive force of the installed cell has come down below the standard level and sends the corresponding result signal to the extension-of-time-setting section. The signal from the comparison-and determination section is also transmitted directly, or indirectly via the extension-of-time-setting section, to the alarm-generating section to generate a predetermined alarm, so that the user is notified that the operative life span for the terminal instrument has lapsed.

Furthermore, the timer mechanism aforementioned may be combined with the above alternative arrangement that is so constructed as no to block the output command while the terminal instrument is being activated.

Thus the present invention further provides a medical apparatus with the above features of (a) to (j) which can make the terminal instrument unusable while the terminal output is being generated when the installed cell is wasted through the use of the terminal instrument beyond a predetermined allowable length of time, which is further characterized in that the extension-of-time-setting section is provided with a timer mechanism which is turned on when the electromotive force of the installed cell has come down below the standard level in (h), and that the primary control section, the allowable-length-of-use-setting/discharging section, the comparison-and-determination section and extension-of-time-setting section are mutually associated in such a manner that the output command being received from the primary control section is transmitted to the terminal-output-generating section without being blocked until the term set by the timer mechanism has lapsed and that, even when the term set by the timer mechanism has lapsed, the output command being received from the primary control section is transmitted to the terminal-output-generating section without being blocked until the output command is once halted.

It is the particular advantage with this apparatus that the terminal instrument can be used for a predetermined length of extra time because of the timer mechanism after the installed cell has been used up during a treatment procedure, and, even when the term set by the timer mechanism has lapsed, the output is not blocked insofar as the terminal instrument is being activated.

Still further, the present invention provides any of the medical apparatus described above which further comprises a checking mechanism so constructed that it, when the output command is not generated, sends to the comparison-and-determination section a voltage-information output corresponding to the electromotive force of the installed cell derived based on the voltage between the cell-voltage-input terminals without causing substantial discharge of the installed cell.

Such a checking mechanism may be incorporated into the allowable-length-of-use-setting/discharging section or provided separately. The specific structure of the checking mechanism is not limited to a particular one. Conveniently, it may be any proper mechanism which, independently from the output command, provides electrical connection between the cell-voltage-input terminals via a resistor with sufficient resistance to avoid any substantial waste of the cell, thus detecting the voltage and sending to the comparison-and-determination section a voltage-information output in the same form as that from the allowable-length-of-use-setting/discharging section.

The medical apparatus with this incorporated checking mechanism is still more useful, for it allows to check the electromotive force of the installed cell well before the output command is set to be generated, i.e., in the step in which the terminal instrument is connected via a cable to the apparatus body, and to promptly know if the operative life span has lapsed with the terminal instrument.

The present invention also provides, in addition to the apparatus body as the component of the above medical apparatus, a medical terminal instrument which has an installed cell and terminals connectable to the cell-voltage-input terminals on the apparatus body and can be used in combination with the apparatus body.

Thus, the present invention provides a medical terminal instrument which operates while receiving from an apparatus body terminal output which may be electric or electromagnetic output, and which is provided with an installed cell of predetermined capacity and further provided with terminals respectively extending from the both poles of the installed cell and electrically connected via a cable to respective cell-voltage-input terminals on the apparatus body.

The terminal instrument of the present invention is characterized in that it is provided, in order to limit its own operative life span, with an installed cell which is discharged while the instrument is being used. The fundamental structure of it as a terminal instrument for one of a variety of medical apparatus such as an apparatus for microwave treatment, electric knife surgery, laser knife surgery or argon beam coagulation, etc., is the same with a conventional corresponding instrument. Therefore, insofar as the apparatus body of the medical apparatus has a function of wasting the cell by discharging it during use in order for determining the total length of use of the terminal instrument, the terminal instrument of the present invention may be used in combination with such a variety of medical apparatus regardless of the manner of determination of the operative life span or the manner of controlling the medical apparatus based on the determination.

BEST MODE FOR CARRYING OUT THE INVENTION

The present invention may be embodied in a variety of apparatus such as an apparatus for microwave surgery, electric knife surgery, laser knife surgery or argon beam coagulation. Therefore, the specific structures of the primary controller, the terminal output generator and the terminal instrument in the present invention are common with the corresponding structures of such a variety of apparatus. Also common to the variety of apparatus is the way of operating the primary controller. Thus, with a microwave surgery apparatus, for example, the primary controller is so constructed that it generates and sends an output command ordering to "generate microwave" to the terminal-output-generating section (microwave generating section in this case) via the extension-of-time-setting section when a foot-switch is stepped on, a coagulation timer is counting down, and no urgent-stop command is received from any one of safety circuits, which are usually included.

The present invention is described in further detail with reference to a representative embodiment, a microwave surgery apparatus. The scope of the present invention, however, is not intended to be limited to the embodiment.

EXAMPLE

Figure 1:
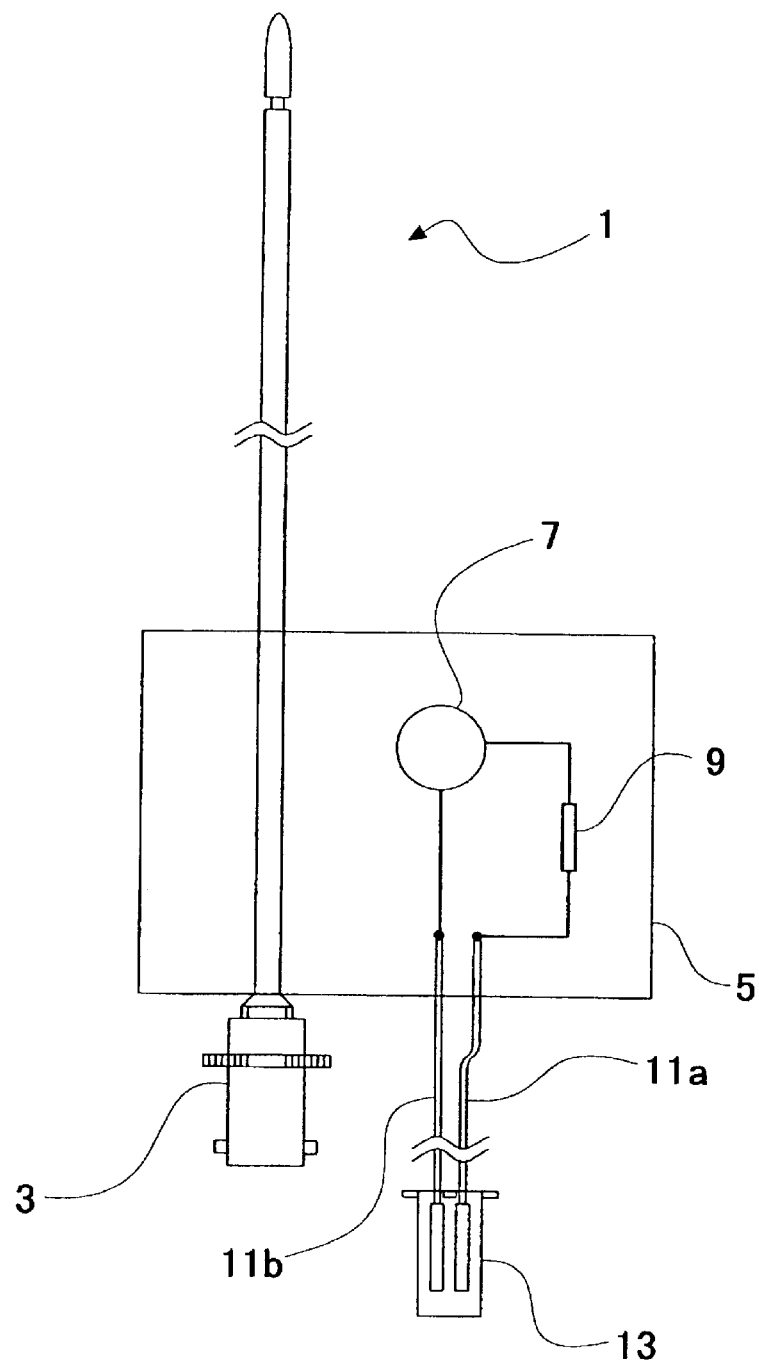
FIG. 1 is a schematic view illustrating the features of the terminal instrument of an embodiment of the present invention.

FIG. 1 is a schematic view illustrating the features of the present invention in a terminal instrument of the embodiment, an electrode for microwave surgery. In the figure, 1 indicates the microwave surgery electrode, which is in this embodiment a well known monopolar electrode. 3 indicates a high-frequency connector, which is connected via a cable (now shown) to the body of the microwave surgery apparatus. The part on a block 5 schematically shows an installed cell and a related circuit, taken out for explanation, which are incorporated in the high-frequency connector 3 of the microwave surgery electrode 1. On the block, 7 indicates an installed cell, which is a small-sized silver oxide cell, for example. One of the poles of the installed cell 7 is connected to one of low voltage terminals 13 via a protective resistor 9 and a conductive wire 11a, and the other of the poles of the installed cell 7 is connected to the other of the low voltage terminals 13 via a conductive wire 11b. The low voltage terminals 13 may be either exposed outside the high-frequency connector 3 or incorporated in the interior of the high-frequency connector 3. In the figure, the low voltage terminals 13 and part of the conductive wires 11a and 11b connected to it are exposed outside the high-frequency connector 3, thus forming a separate set of terminals independent from the high-frequency connector 3.

Figure 2:
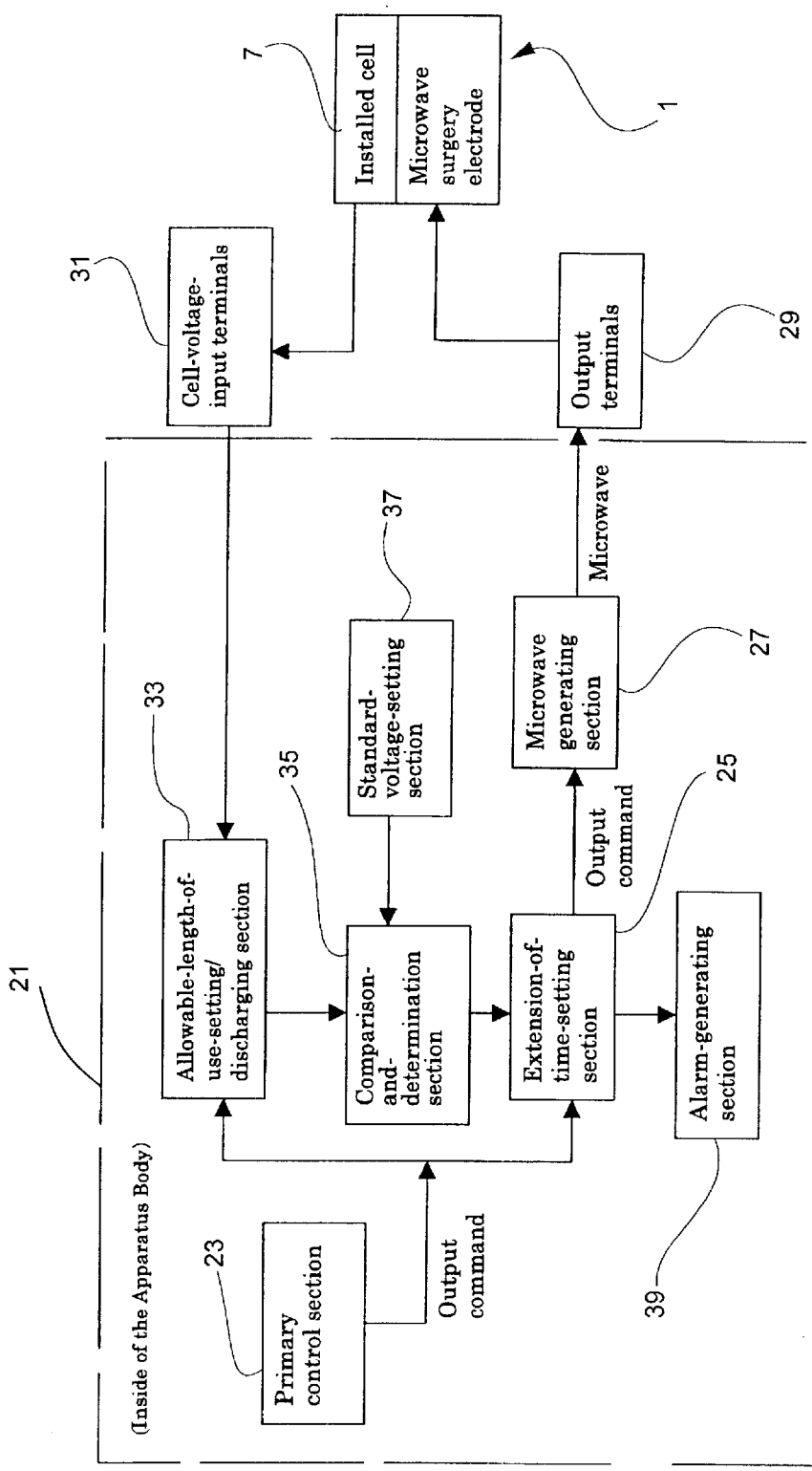
FIG. 2 is a block diagram showing the structure of the embodiment of the medical apparatus.

FIG. 2 is a block diagram showing the structure of the embodiment of the present invention. In the figure, 21 indicates the apparatus body. A microwave output command generated by a primary control section 23 in the apparatus body 21, if not blocked by an extension-of-time-setting section 25, is transmitted to a microwave generating section (consisting of a microwave generator) 27 via the extension-of-time-setting section, and microwave generated by the microwave generating section 27 is led to the microwave surgery electrode 1 via the cable connected to output terminals 29 and via the high-frequency connector 3.

On the other hand, the conducting wires extending from the both poles of the installed cell 7 of the microwave surgery electrode 1 are connected to the cell-voltage-input terminals 31 on the apparatus body 21 via the low voltage terminals 13 and via the cable, and then communicating with an allowable-length-of-use-setting/discharging section 33. The allowable-length-of-use-setting/discharging section 33 operates upon receipt of the output command from the primary control section 23 to close the circuit including the installed cell 7 illustrated in FIG. 1 via a resistor R with predetermined resistance, which may be a variable resistor, provided in the allowable-length-of-use-setting/discharging section 33, to continuously discharge the installed cell 7. At the same time, the allowable-length-of-use-setting/discharging section 33 measures the voltage between the both ends of the resistor and determines the electromotive force of the installed cell 7 on the basis of the fractions of resistance of the circuit including the internal resistance of the installed cell 7 and the resistance of the protective resistor 9, and transmits corresponding voltage, which is the voltage-information output, to a comparison-and-determination section 35. The comparison-and-determination section 35 receives this voltage-information output as well as a reference voltage from a standard-voltage-setting section 37 that provides the criterion for determining about the waste of the installed cell 7, and determines whether or not the electromotive force of the cell is still on or above the standard level. The comparison-and-determination section 35 outputs the result of the determination for the extension-of-time-setting section 25.

The allowable-length-of-use-setting/discharging section 33 also has a checking mechanism which so functions that it, in the step in which the microwave surgery electrode 1 is attached prior to use to the apparatus body via the cable, closes a circuit including the installed cell 7 illustrated in FIG. 1 via a resistor which is different from and has far greater resistance than the above-mentioned resistor R to measure the electromotive force of the installed cell 7 without wasting it and transmits corresponding voltage, which is the voltage-information output, to the comparison-and-determination section 35. The checking mechanism is so constructed that it does no require for its operation the output command from the primary control section 23, and therefore it can check the installed cell 7 immediately after the microwave surgery electrode 1 is connected. The comparison-and-determination section 35 compares the voltage-information output from the checking mechanism with the voltage-information output from the standard-voltage-setting section 37, thereby determines whether or not the electromotive force of the installed cell 7 is below the standard level, and outputs the result signal for the extension-of-time-setting section 25.

An alarm-generating section 39 receives signals from the comparison-and-determination section 35 via the extension-of-time-setting section 25 and generates an alarm corresponding to levels of the electromotive force of the installed cell 7. An optical as well as auditory alarm is given by a lamp turned on and a signal sound.

Before the activation of the microwave generating section 27, the extension-of-time-setting section 25, upon receipt of the output command from the primary control section 23, transmits the output signal to the microwave generating section 27 (ON) if the result signal from the comparison-and-determination section 35 is the one indicating that the electromotive force of the installed cell is on or above the standard voltage at which the use of the microwave surgery electrode 1 is allowed. On the contrary, if the result signal from the comparison-and-determination section 35 is the one indicating that the electromotive force of the installed cell 7 has come down below the standard voltage at which the use of the microwave surgery electrode 1 is allowed, the output command is blocked and not transmitted to the microwave generating section 27 (OFF).

When the microwave generating section 27 is already in operation, extension-of-time-setting section 25 transmits the output command to the microwave generating section 27 (ON) as long as the result signal from the comparison-and-determination section 35 is the one indicating that the electromotive force of the installed cell 7 is on or above the standard voltage at which the use of the microwave surgery electrode 1 is allowed. On the contrary, if the result signal from the comparison-and-determination section 35 is the one indicating that the electromotive force of the installed cell 7 has come down below the standard voltage at which the use of the microwave surgery electrode 1 is allowed, the extension-of-time-setting section 25 activates a timer and transmits the output command to the microwave generating section 27 (ON maintained) without blocking it until the term of three minutes originally set in the timer has lapsed regardless of the signal from the comparison-and-determination section 35, and then blocks the output command at the same time when the set term has just lapsed. As mentioned above, if the result signal from the comparison-and-determination section 35 is the one indicating that the electromotive force of the installed cell 7 has come down below the standard voltage at which the use of the microwave surgery electrode 1 is allowed, the signal is also transmitted to the alarm-generating section and therefore the user is notified with the activated optical and auditory alarm that the remaining time is being counted down during which the use of the microwave surgery electrode 1 is allowed.

Figure 3:
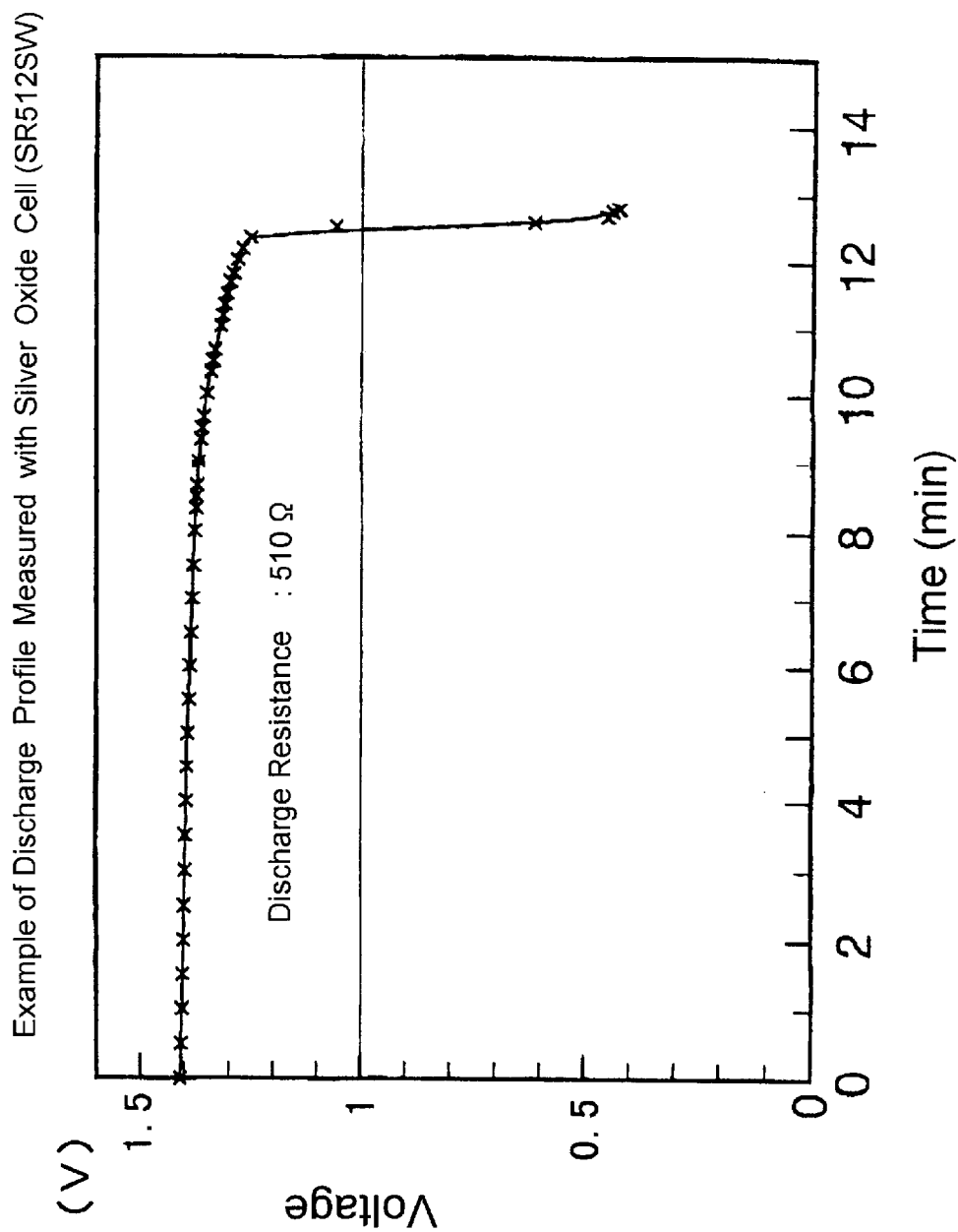
FIG. 3 is a graph illustrating a discharge profile of a silver oxide cell.

FIG. 3 is a graph which shows the discharge profile of a silver oxide cell (SR512SW) used as the installed cell 7, in which graph the vertical axis represents the cell voltage and the horizontal axis the time lapse (in minutes) from the start of discharge. In this example, with an employed discharge resistor of 510Ω, it is seen in FIG. 1 that the cell is used up in about 12 minutes, but its voltage is kept rather stable just before the final use up. As an abrupt lowering in the cell voltage occurs only just before the complete use up, quite easy and reliable determination of when the cell is used up is possible by comparison with a standard voltage of 1 V, for example, using a simple circuit.

The aforedescribed sections such as sections 23, 25, 27, 33, 35 and 37 provide an enabling circuit which does not enable or precludes operation of the terminal instrument 1 if the cell for battery has a reduced capacity indicating a single use of the terminal instrument.

Figure 4:
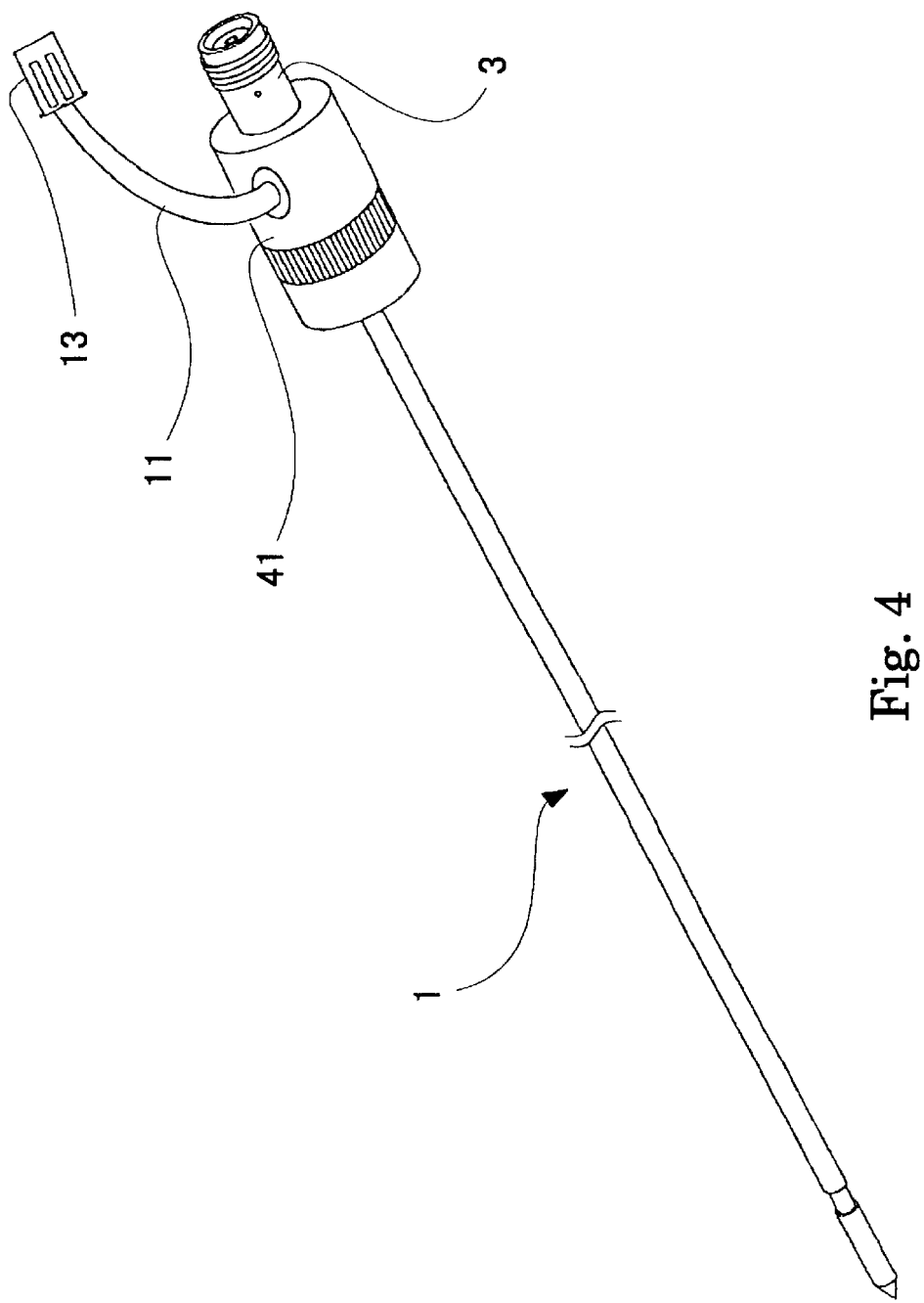
FIG. 4 is a perspective view illustrating the outlook of an embodiment of the terminal instrument.

FIG. 4 is a perspective view of the outlook of an embodiment of the terminal instrument, microwave surgery electrode 1. In the figure, the installed cell 7 and the protective resistor 9, both illustrated in FIG. 1, are placed inside the handle 41 of the microwave surgery electrode 1. From the lateral surface of the handle 41 extend the conductive wires 11, at the end of which is attached low voltage terminals 13. In use, the high-frequency connector 3 is connected to the end of the predetermined cable which in turn is connected to the apparatus body 1. The cable is provided with distal terminals to be connected to the low voltage terminals 13 and proximal terminals connected to the distal terminals via conductive wires through the cable. By connecting the proximal terminals to the cell-voltage-input terminals 31, connection is established between the installed cell 7 and the allowable-length-of-use-setting/discharging section 33.

In the example shown in FIG. 4, the low voltage terminals 13 are provided as a separate part from the high-frequency connector 3 and exposed outside. However, they may be formed into an integral connector.

INDUSTRIAL APPLICABILITY

The present invention enables to provide a medical instrument and medical apparatus equipped with it for microwave surgery, electric knife surgery, laser knife surgery, argon beam coagulation, etc., wherein the medical instrument is made so that it can substantially force itself to be disposed of after use through restricting, without adversely affecting its quality or safety of the apparatus, the length of time during which the use of the medical instrument is allowed.

What is claimed is:

1. A medical apparatus comprising:
 a terminal instrument and an apparatus body, wherein the apparatus body comprises
 a terminal-output-generating section for generating predetermined terminal output for activating the terminal instrument, wherein the terminal output is an electric or electromagnetic output and
 a primary control section for sending an output command that when received by the terminal-output-generating section activates the terminal-output-generating section to generate terminal output, and
 wherein the terminal instrument is removably connected via a cable to the terminal-output-generating section and activated by the terminal output,
 (1) wherein the terminal instrument is provided with an installed cell having a predetermined capacity and further with terminals respectively extending from the both poles of the installed cell and electrically connected via a cable to corresponding cell-voltage-input terminals on the apparatus body, and
 (2) wherein the apparatus body further comprises:
   (a) an allowable-length-of-use-setting/discharging section that is activated upon receipt of the output command from the primary control section,
   an extension-of-time-setting section that is activated upon receipt of the output command from the primary control section,
   a comparison-and-determination section,
   a standard-voltage-setting section for providing the comparison-and-determination section with standard-voltage information for reference, and
   an alarm-generating section,
   (b) wherein the allowable-length-of-use-setting/discharging section is so constructed that it, upon receipt of the output command, establishes electrical communication between the cell-voltage-input terminals via a predetermined resistor to form a closed circuit to discharge the installed cell and thereby keeps the installed cell being discharged while the terminal-output-generating section is activated by the output command transmitted thereto to generate terminal output, and that it sends a cell voltage-information output corresponding to the electromotive force of the installed cell determined based on the voltage between two different points along the circuit, to the comparison-and-determination section,
   (c) wherein the comparison-and-determination section is so constructed that it compares the voltage-information output with the standard-voltage information it has received from the standard-voltage-setting section to determine whether the electromotive force of the installed cell is equal to or greater than the standard voltage or has fallen below the standard voltage, and then sends the result signal to the extension-of-time-setting section as well as to the alarm-generating section,
   (d) wherein the extension-of-time-setting section is so constructed that it, depending on the result signal it has received from the comparison-and-determination section, transmits the output command from the primary control section to the terminal-output-generating section if the electromotive force of the installed cell is equal to or greater than the standard voltage but can block the transmission of the output command if the electromotive force of the installed cell is below the standard voltage, and
   (e) wherein the alarm-generating section is so constructed that it, according to the result signal it has received from the comparison-and-determination section, generates an alarm signal if the electromotive force of the installed cell is lower than the standard voltage.

2. The medical apparatus of claim 1 further characterized in that:

(g) the extension-of-time-setting section is so constructed that it, while the output command from the primary control section is transmitted to the terminal-output-generating section and the terminal-output-generating section is thereby generating terminal output, continually sends the voltage-information output corresponding to the electromotive force of the installed cell to the comparison-and-determination section, (h) the comparison-and-determination section is so constructed that it compares the voltage-information output it is continually receiving with the standard-voltage information from the standard-voltage-setting section, thereby continually determines whether the electromotive force of the installed cell is equal to or greater than the standard voltage or has come down below the standard voltage, and transmits the result signal to the extension-of-time-setting section and the alarm-generating section, (i) the extension-of-time-setting section is so constructed that it, upon receipt of the signal in (h), continues to transmit the output command from the primary control section to the terminal-output-generating section if the electromotive force of the installed cell is equal to or greater than the standard voltage, but can block the output command if the electromotive force of the installed cell has come down below the standard voltage, and (j) the alarm-generating section is so constructed that it, according to the signal in (h), can generate an alarm signal indicating when the electromotive force of the installed cell has come down below the standard voltage.

3. The medical apparatus of claim 2 further characterized in that the extension-of-time-setting section is provided with a timer which is started when the electromotive force of the installed cell has come down below the standard voltage in (h) and the extension-of-time-setting section is so constructed that it continues to transmit the output command from the primary control section to the terminal-output-generating section even after receiving from the comparison-and-determination section a result signal indicating that the electromotive force of the installed cell has come down below the standard voltage in (h), until the term set by the timer has lapsed.

4. The medical apparatus of claim 2 further characterized in that the extension-of-time-setting section is so constructed that it continues to transmit the output command from the primary control section to the terminal-output-generating section even after receiving from the comparison-and-determination section a result signal indicating that the electromotive force of the installed cell has come down below the standard voltage in (h), until the output command is once halted.

5. The medical apparatus of claim 3 further characterized in that the extension-of-time-setting section is so constructed that it continues to transmit the output command from the primary control section to the terminal-output-generating section even after the term set by the timer mechanism has lapsed, until the output command is once halted.

6. The medical apparatus of claim 1 further comprising a checking mechanism so constructed that it, when the output command is not generated, sends to the comparison-and-determination section a voltage-information output corresponding to the electromotive force of the installed cell which is determined based on the voltage between the cell-voltage-input terminals without causing substantial discharge of the installed cell.

7. The medical apparatus of claim 1 which is an apparatus for microwave surgery, electric knife surgery, laser knife surgery or argon beam coagulation.

8. The medical apparatus of claim 6 which is apparatus for microwave surgery, electric knife surgery, laser knife surgery or argon beam coagulation.

9. The medical apparatus of claim 1 wherein the installed cell is a silver oxide cell.

10. The medical apparatus of claim 6 wherein the installed cell is a silver oxide cell.

11. A terminal instrument which is activated by terminal output from the apparatus body of claim 1 and provided with an installed cell having a predetermined capacity and further with terminals respectively extending from the both poles of the installed cell and electrically connected via a cable to corresponding cell-voltage-input terminals on the apparatus body.

12. The terminal instrument of claim 11 which is a terminal instrument for apparatus for microwave surgery, electric knife surgery, laser knife surgery, or argon beam coagulation.

13. The terminal instrument of claim 11 wherein the installed cell is a silver oxide cell.

14. The terminal instrument of claim 12 wherein the installed cell is a silver oxide cell.

15. A medical terminal instrument for detachable connection as a unit to an enabling circuit, the medical terminal instrument being actuated by electric or electromagnetic current and being provided with an installed cell integral therewith, the installed cell having a predetermined electrical capacity and a pair of poles; the medical terminal being further provided with terminals extending from both poles of the installed cell for electrical connection outside of the medical terminal instrument to the enabling circuit; whereby if the electrical capacity of the cell is less than a selected level, operation of the medical terminal instrument is not enabled.

16. A medical terminal instrument which is activated by electric or electromagnetic current, the medical terminal instrument being provided with an installed cell having a pair of poles and a predetermined capacity and being further provided with terminals extending from the poles of the installed cell for electrical connection outside the medical terminal instrument, wherein the installed cell is a battery having a predetermined electrical capacity which is reduced by a single use of the terminal instrument and wherein the poles are connectable to an enabling circuit for sensing a reduction from the predetermined electrical capacity and for precluding operation of the terminal instrument if the reduction in electrical capacity indicates a single use of the terminal instrument.

17. The terminal instrument of claim 16 which is a terminal instrument for apparatus for microwave surgery, electric knife surgery, laser knife surgery, or argon beam coagulation.

18. The terminal instrument of claim 17 wherein the installed cell is a silver oxide cell.

* * * * *